United States Patent [19]

Wilson, III

[11] Patent Number: 5,361,779
[45] Date of Patent: Nov. 8, 1994

[54] TUBULAR SHEATHING ARTICLE COMPRISING KNITTED RETENTION STRUCTURE, AND METHOD OF MAKING THE SAME

[75] Inventor: Thomas W. Wilson, III, Chapel Hill, N.C.

[73] Assignee: Family Health International, Research Triangle Park, N.C.

[21] Appl. No.: 978,348

[22] Filed: Nov. 18, 1992

[51] Int. Cl.$^5$ .............................. A61F 6/02; A61F 6/04
[52] U.S. Cl. ..................... 128/842; 128/844; 128/918
[58] Field of Search ............... 128/842, 844, 918, 830; 604/330, 347–353

[56] References Cited

U.S. PATENT DOCUMENTS

| | | |
|---|---|---|
| D. 253,009 | 9/1979 | Okamoto . |
| 1,113,561 | 10/1914 | Jorgenson . |
| 2,138,626 | 11/1938 | Copen ................................ 128/844 |
| 2,285,981 | 6/1942 | Johns . |
| 2,305,453 | 12/1942 | Martos . |
| 2,389,831 | 11/1945 | Welsh . |
| 2,410,460 | 11/1946 | Robinson . |
| 2,433,538 | 12/1947 | Warner . |
| 2,484,356 | 10/1949 | Ribeiro et al. . |
| 2,488,938 | 9/1948 | Wayne . |
| 2,577,345 | 12/1951 | McEwen . |
| 2,586,674 | 2/1952 | Lonne . |
| 2,604,092 | 7/1952 | Brown . |
| 2,610,630 | 9/1952 | Crew ................................ 604/347 |
| 2,670,736 | 3/1954 | Dundelberger . |
| 2,904,041 | 9/1959 | Brown . |
| 3,037,508 | 6/1962 | Freidman . |
| 3,149,017 | 9/1964 | Ehririch et al. . |
| 3,295,145 | 1/1967 | Erickson . |
| 3,361,857 | 1/1972 | Maddison . |
| 3,588,997 | 6/1971 | Field . |
| 3,631,857 | 1/1972 | Maddison . |
| 3,759,254 | 9/1973 | Clark . |
| 3,992,766 | 11/1976 | Field . |
| 4,004,591 | 1/1977 | Freimark . |
| 4,009,717 | 3/1977 | Allen . |
| 4,022,213 | 10/1977 | Stein . |
| 4,100,309 | 7/1978 | Micklus . |
| 4,232,675 | 11/1980 | Neldahl . |
| 4,241,828 | 12/1980 | Bourdelle et al. . |
| 4,275,812 | 6/1981 | Poncy . |
| 4,354,494 | 10/1982 | Hogan . |
| 4,432,357 | 2/1984 | Pomeranz . |
| 4,446,860 | 5/1984 | Gutnick . |
| 4,475,910 | 10/1984 | Conway et al. . |
| 4,484,918 | 11/1984 | Omley . |

(List continued on next page.)

FOREIGN PATENT DOCUMENTS

| | | | |
|---|---|---|---|
| 657004 | 2/1963 | Canada ................................ 604/349 |
| 0147072 | 7/1985 | European Pat. Off. . |
| 2020280 | 11/1971 | Germany . |
| 2349361 | 4/1975 | Germany . |
| 1595711 | 8/1981 | United Kingdom . |
| 2225721 | 6/1990 | United Kingdom ................. 128/844 |
| 8402070 | 6/1984 | WIPO ................................ 604/349 |

*Primary Examiner*—Michael A. Brown
*Attorney, Agent, or Firm*—Steven J. Hultquist

[57] ABSTRACT

A generally loose-fitting tubular sheath article, such as a condom, which has a closed distal end and an open proximal end which is bounded by a knitted material that bears compressively on the sheathed member to provide retention. The knitted material may be in the form of a band which is affixed to the sheath by everting a portion of the sheath material at the proximal end over the knitted material and attaching the sheath material to itself, thereby creating a toroidal enclosure in which the knitted material is disposed. Constriction of the sheathed member is minimized by the knitted material which provides a large surface area for retentive contact.

14 Claims, 4 Drawing Sheets

U.S. PATENT DOCUMENTS

| | | |
|---|---|---|
| 4,576,156 | 3/1986 | Dyke . |
| 4,601,716 | 7/1986 | Smith .................................... 604/349 |
| 4,626,250 | 12/1986 | Schneider . |
| 4,664,104 | 5/1987 | Jaicks . |
| 4,684,490 | 8/1987 | Taller . |
| 4,735,621 | 4/1988 | Hessel . |
| 4,781,709 | 11/1988 | Grubman . |
| 4,794,929 | 1/1989 | Robichaud . |
| 4,795,425 | 1/1989 | Rugh . |
| 4,796,600 | 1/1989 | Meadows . |
| 4,805,604 | 2/1989 | Spery . |
| 4,808,174 | 2/1989 | Sorkin . |
| 4,834,114 | 5/1989 | Boarman ............................. 128/844 |
| 4,872,464 | 10/1989 | Loeb et al. . |
| 4,875,490 | 10/1989 | Quiroz . |
| 4,885,169 | 8/1989 | McGlothlin et al. . |
| 4,888,007 | 12/1989 | Loeb et al. . |
| 4,926,851 | 5/1990 | Bulley .................................... 602/76 |
| 4,942,885 | 7/1990 | Davis et al. . |
| 4,955,392 | 9/1990 | Sorkin . |
| 4,964,416 | 10/1990 | Foldesy et al. . |
| 4,966,166 | 10/1990 | Leffler . |
| 4,971,071 | 11/1990 | Johnson ............................. 604/347 |
| 4,971,074 | 11/1990 | Hrubetz ............................. 604/349 |
| 4,993,433 | 2/1991 | Reddy . |
| 5,121,755 | 6/1992 | Hegedusch ........................ 128/844 |
| 5,163,448 | 11/1992 | Foldesy . |

TUBULAR SHEATHING ARTICLE COMPRISING KNITTED RETENTION STRUCTURE, AND METHOD OF MAKING THE SAME

BACKGROUND Of THE INVENTION

1. Field of the Invention

This invention relates to a generally tubular sheathing article, e.g., a condom or prophylactic article, comprising a knitted retention structure for compressively retaining the sheathing article on the member or element being sheathed, as well as to a method of making such sheathing articles.

2. Description of the Related Art

In the field of prophylactic or condom articles, much effort has been directed in recent years to improving the structure and rate of fabrication of such articles, under the impetus of significant increases in the incidence and spread of sexually transmitted diseases, as a result of the evolution of increasingly antibiotic-resistant strains of disease-causing organisms, e.g., those responsible for diseases such as gonorrhea and syphilis, and the absence of any effective cure for acquired immunodeficiency syndrome (AIDS).

The aforementioned disease factors have also created an increased consumer demand for condoms, in view of their benefits as a safe, low cost, and generally reliable means for reducing the risk of infection and transmission of sexually transmitted diseases, as well as their traditional function as a barrier-type contraceptive means.

Against this background, design and manufacturing efforts have been focused on the develop of condoms characterized by increased ease of application to the penis of the wearer, and comfort in use, to thereby enhance the appeal of using condoms in coital activity.

Currently, most condoms are produced from a latex resin via a dipping process in which a cylindrical and rounded-end mold is dipped into a resin bath, so that the mold is coated with a thin layer of the latex material. The thickness of the latex coating on the mold is dependent on the viscosity of the latex, and the speed of extracting the mold from the latex bath. Similar latex dipping processes have been employed with suitably shaped molds to form tight-fitting gloves such as surgical gloves, as well as other sheathing articles.

Structurally, the conventional latex condom comprises a tubular main sheath with a closed distal end and an open proximal end. The open proximal end may be circumscribingly bounded by a filament of elastic material, to aid in retaining the condom on the penis of the wearer, to demarcate the proximal opening for use of the condom, and to prevent tearing of or damage to the tubular main sheath of the condom during its application and use.

In addition, the circumscribing filament serves as a "rolling core" onto which the main sheath portion of the condom may be rolled along its length in conventional fashion to produce a toroidal roll surrounding a distal end portion of the sheath when the condom is in a fully rolled conformation; subsequently, the condom is simply reverse-rolled onto the penis of the wearer, from the glans to the base of the penis.

To the extent that the elastic filament bears compressively against the circumference of the base of the penis, a further enhanced protection is provided against leakage of seminal fluid and sperm from the condom, and against entry of vaginal exudates or other coital secretions from the recipient coital partner, into the interior volume of the condom containing the penis, during sexual activity.

In order to accommodate the sealing and retention function of the elastic filament at the proximal opening of the condom, the elastic filament must be significantly stretched in application of the condom to the wearer's penis. As a result, the condom is often difficult to don, due to the small size of the condom's proximal opening, and the resistance to stretching of the proximal opening and the bounding filament which is intended to provide a tight fit once the condom is installed on the penis of the wearer.

During their commercial production, condoms made of latex rubber typically are rolled, as hereinabove discussed, to render them easier to package, store, and apply, relative to unrolled condoms. Although rolling gives the condom a more compact structure, thereby facilitating ease of packaging and storage, the donning of rolled condoms frequently is difficult since the user must stretch the roll apart in the donning operation. Generally, the "spreadability" of the rolled condom is made difficult by its tightly compacted character, and the required positioning of the rolled condom on the invariably asymmetric glans of the penis to initiate unrolling.

Further, the roll portion of the condom initially must be grasped with the fingers for application to the glans and unrolling onto the penis. The size of the condom roll is typically sufficiently small, e.g., generally being less than about 3/16 inch in roll diameter, so that it is difficult to grasp the roll with the fingertips and to install the condom on the penis of the wearer. This is particularly true in the case of very thin or form-fitting condoms which are characterized by a very tiny roll.

As a result of the small size (diameter) of the roll, the need to utilize the fingers in installation of the condom, and the absence of good grippability, the fingertips are often tightly pinched onto the roll to gain purchase thereon. This in turn raises the risk of shredding or puncturing of the condom material by the fingernails or otherwise breaking the condom as a result of such pinching or grasping, so that the condom, when subsequently unrolled, has breaks or discontinuities therein which render the condom deficient or even useless for its intended function.

The foregoing problems attendant to the use of conventional rolled condoms with elastic filament retaining rings has stimulated the development of alternative condom designs, wherein the retention structure is of a different type than elastic filaments. This effort has been made in the context of an evolution of condom technology to embrace the use of materials of construction other than latex rubber for the condom sheath.

Wheeler U.S. Pat. No. 4,964,416 discloses condoms formed of thermoplastic elastic materials such as thermoplastic elastomers, e.g., polyurethanes, polyesters, polyethers, multi-block copolymers, olefinic homopolymers and copolymers, etc. This patent discloses the use of an annular sealing element at the proximal end portion of the condom which features a circumscribed opening bounded by the annular body of the sealing element. The sealing element is formed of a thin film material, so that when the condom is donned, the inner edge surface of the annular element opening bears compressively on the external surface of the base of the penis, to provide enhanced sealing thereagainst.

Although the Wheeler patented condom provides an effective seal against the exterior surface of the penis, and the interior opening of the annular sealing element permits ready passage of the penis therethrough when the condom is installed on the penis, after installation the compressive retention force is applied to the surface of the penis only over the inner circumferential surface of the thin film annular sealing element. As a result the compressive pressure of the annular sealing element on the penis is substantial, and although the thin film annular element is radially and circumferentially yielding in character, the constrictive force exerted by the sealing element may exceed the limit of comfort, particularly when the penis being sheathed is significantly larger in circumference than the inner opening of the annular sealing element.

Considering as illustrative examples the above-discussed elastic filament retention structures of conventional latex condoms, and the annular sealing element of the Wheeler patent, it is appreciated that the compressive retention structure of a condom must satisfy several competing criteria:

(1) the retention structure must provide adequate compressive force on the penis for effective sealing of the sheath of the condom against leakage into or out of the condom sheath interior volume containing the penis, such as may compromise the contraceptive and/or prophylactic efficacy of the condom;

(2) the retention structure must allow ready ingress of the penis into the sheath of the condom, which means that the retention structure must be expandable from its initial compressive or gathered state to permit the condom to be easily rolled or pulled onto the penis for installation thereon;

(3) the retention structure must provide a constrictive action which however does not produce discomfort or otherwise interfere with coital pleasure and satisfaction; and (4) the retention structure must be readily securable to or formable with the sheath structure of the condom, so that the condom can be easily, quickly, and economically produced in mass production quantities—it is to be recognized that the compressive retention structure is desirably structurally consolidated with the sheath of the condom, as a unitary product article, during the condom manufacturing process, and this typically involves expansion of the retention structure prior to and/or during its being joined with the sheath, followed by relaxation of the stretched retention structure.

Considering the manufacturability factors identified in (4) above, it is apparent that the stretching of a small diameter elastic filament or 0-ring for connection to the sheath presents significant processing problems. In conventional latex condom manufacture, the retention ring is stretched over the mandrel bearing the latex sheath member (formed by drying of the latex solution applied to the mandrel during dipping thereof, as previously described hereinabove), and is positioned at a proximal part of the sheath. The condom then is rolled on the mandrel, about the elastic filament as a rolling core. In the rolling operation, a portion of the ring or resultingly formed roll may, during the rolling operation, preferentially grip or gain purchase on, the film, so that uneven tension is imposed on the sheath, which may cause it to subsequently tear or split in use. Further, the generally circular cross-section of the elastic filament and its typically very small diameter make it very difficult to gain purchase on and to position or translate with high accuracy (these are the manufacturing analogs of the purchase/manipulability use problems discussed earlier hereinabove), and these factors again may lead to the aforementioned uneven rolling problems.

The above-described Wheeler patented condom avoids the aforementioned problems incident to the use of the elastic filament as a compressive retention structure, but presents its own difficulties in the handling and processing of the thin film annular sealing element, which must of course be leak-tightly secured to the inner surface of the condom sheath to achieve its intended purpose. The thickness of the annular thin film sealing element may for example be commensurate with the thickness of the sheath itself, and leak-tight sealing of such low thickness films requires very accurate sealing techniques, such as heat sealing or ultrasonic bonding at low dimensional tolerances, which avoid the rupture or piercing of the films during their bonding to one another.

U.S. Pat. No. 4,855,169 issued Aug. 8, 1989 to M. W. McGlothlin et al., describes a prophylactic device including a sheath of elastomeric sheet material with a 100% tensile modulus of at least about 200 psi and a thickness of less than about 0.0014 inch. The sheath has an open end and a border containing a resilient material of reduced 100% tensile modulus, relative to the elastic sheet material. In this device, the ratio of the thickness of the border to the thickness of the sheath is from about 10 to about 300. The materials disclosed in the patent for the sheath include polyurethane and various other thermoplastic elastomeric materials. The patent discloses that the border may be constituted by a ring which is either bonded or unbonded to the sheath, or, alternatively, the border may be constituted by a flat band encircling the proximal open end of the sheath of either bonded or unbonded type.

The McGlothlin et al. patent discloses that the augmented border which is provided as the retention structure of the described prophylactic article may be formed of low modulus materials such as polyurethanes, plasticized polyurethanes, latex rubbers, silicone elastomers, ethylene/propylene thermoplastic elastomers, styrene block copolymer thermoplastic elastomers, olefinic thermoplastic elastomers, polyether block amide thermoplastic elastomers, polyvinylchlorides, acrylic-based thermoplastic elastomers, hot-melt or pressure adhesive materials, and foam polymers.

An improvement on the condom of the McGlothlin patent is disclosed in prior copending patent application Ser. No. 07/693,550 filed Apr. 30, 1991 in the name of John T. Leffler. This application discloses a condom comprising an elongate sheath having an open proximal end and a closed distal end, which is rolled or rollable on a roll ring having an axial thickness dimension and a transverse (width) dimension each of which is at least 0.125 inch, wherein the thickness of the sheath is from about 0.0004 inch to about 0.003 inch, and the ratio of the transverse width of the roll ring to the thickness of the sheath is in the range of from about 350 to about 5,000. The roll ring in such condom structure may be of a low durometer material such as a highly plasticized or solvent-swollen polymer having a gelatinous consistency rendering the sheath easily rollable thereon.

While the thrust of the teachings of the aforementioned McGlothlin et al. patent and Leffler patent application are in favor of relatively large roll rings or band structures as rolling cores, having a number of intrinsic advantages as described in these references, there is a continuing need in the art for compressive retention structures of improved type, which afford the various advantages taught to be characteristic of the McGlothlin et al. and Leffler ring and band retention structures, but which are more compact in size, and which fully meet the criteria (1)–(4) referred to and discussed hereinabove.

Accordingly, it is an object of the present invention to provide a sheath article having a compressive retention structure of improved type, affording such aforementioned advantages.

It is another object of the invention to provide a sheath article of such type, which is easily, simply, and economically manufacturable in character.

It is a still further object of the present invention to provide a method of making an improved sheath article of such type.

Other objects and advantages of the present invention will be more fully apparent from the ensuing disclosure and appended claims.

SUMMARY OF THE INVENTION

In one aspect, the present invention relates to a generally tubular sheath article comprising a main sheath defining an interior volume therewithin, and including a closed distal (or first) end and an open proximal (or second) end, having associated with the open proximal end a knitted web retention member which is constructed and arranged to bear compressively on a sheathed part reposed in the interior volume of the main sheath.

The knitted web retention member may for example be in the form of a continuous circumferential band or cylindrical collar, or may include single or multiple, partially circumferentially extending retention element(s) which serve to provide the compressive retention function for the tubular sheath article.

In a specific aspect, the invention relates to a sheathing article for protective covering of a sheathable part, comprising:

(i) a generally tubular sheath member having a closed first end and an open second end defining an enclosed interior volume within the sheath member accessible by the open second end, for introduction of the sheathable part into the interior volume through the open second end; and (ii) a knitted retention structure associated with the sheath member at a proximal portion of the sheath member in the vicinity of its open second end, for exerting a compressive retaining action on the sheathable part at the proximal portion of the sheath member.

In such article, the knitted retention structure may comprise a knitted web strip circumferentially extending at least partially about the exterior surface of the sheath member at its proximal portion, e.g., a knitted material band circumscribing the exterior surface of the sheath member at its proximal portion.

In a preferred aspect, the knitted material band may be reposed in a circumferentially extending proximal compartment at the proximal portion of the sheath member, wherein the proximal compartment comprises an exteriorly everted skirt segment of sheath member secured to the exterior surface of the sheath member to define an internal compartment volume containing the knitted material band.

The knitted retention structure may suitably comprise yarn selected from the group consisting of: staple yarns; filament yarns; and combinations thereof, e.g., elastomeric yarn, formed of a material selected from the group consisting of rubber, spandex, copolyetheresters, texturized nylon, and combinations thereof, or, more broadly, of a material selected from the group consisting of: acrylics; polyesters; polyamides; rayon; cellulose acetates; silk; wool; cotton; polypropylene; polyurethane; copolyetherester; rubber; polyvinyl chloride; polyvinylidene chloride; polyvinyl alcohol; linen; flax; polyethylene; polyaramide; spandex; copolymers of monomers of said polymers; and composites, combinations, and multicomponent forms thereof.

The knitted retention structure may comprise a needle-knitted tubular material fabricated with a needles per course characteristic of from 56 to 110 needles per course, preferably from 76 to 90 needles per course.

In one particularly preferred embodiment, the knitted retention structure comprises a knitted band characterized by: an Equivalent Diameter Garter Force Value of from about 0.04 to about 0.06 kilograms at 33 millimeters and from about 0.60 to about 0.90 kilograms at 48 millimeters; a Mandrel Retention Force Value of from about 0.30 to about 0.35 kilograms; and a Relaxation Creep Value of from about 10% to about 40% over a strain of range from 30% to 130%.

The sheath material of the article of the invention may usefully comprise a material selected from the group consisting of: polyurethanes; latex rubbers; silicone elastomers; ethylene-propylene thermoplastic elastomers; styrene block copolymer thermoplastic elastomers; olefinic thermoplastic elastomers; polyether block amide thermoplastic elastomers; polyvinyl chlorides; and acrylic-based thermoplastic elastomers.

In another aspect, the present invention relates to a method of making a sheathing article, comprising:

(a) providing a generally tubular sheath member having a closed first end and an open second end;
(b) disposing a circumferentially extending knitted retention band about an exterior surface second end portion of the sheath member, in spaced relation to the open second end thereof, to thereby define a proximal segment of the sheath member between the knitted retention band and the open second end;
(c) everting the proximal segment of the sheath member between the knitted retention band and the open second end so that the everted proximal segment enclosingly overlies the knitted retention band; and
(d) securing the everted proximal segment of the sheath member to an overlaid exterior surface region of the sheath member to form an enclosure volume containing the knitted retention band.

DETAILED DESCRIPTION OF THE INVENTION AND PREFERRED EMBODIMENTS THEREOF

The present invention is based on the discovery that a knitted web retention structure may be employed at the proximal or open end of a generally tubular sheath article, such as a condom or prophylactic device, and is usefully employed to bear compressively on a sheathed part, such as a penis in the case of a prophylactic or condom article, which is reposed in the interior volume of the main sheath portion of such article.

Thus, the generally tubular sheath article may comprise a main sheath defining the aforementioned interior volume therewithin, including a closed distal (or first) end and an open proximal (or second) end, wherein the knitted web retention structure is associated with the open proximal end.

It is surprising and unexpected that knitted web materials may be thus employed as retention elements for such generally tubular sheath articles, which are typically formed of latex, thermoplastic elastomers, or other flexible, resilient materials of construction.

The knit material employed in the knitted retention structure can be fabricated from staple and/or filament yarns. Illustrative of suitable materials for the yarns are the following materials: acrylics, polyesters, polyamides (nylons), rayon, cellulose acetates, silk, wool, cotton, polypropylene, polyurethanes, copolyetheresters, rubbers, polyvinylidene chloride and its copolymers, polyvinyl chloride and its copolymers, polyvinyl alcohol and modified forms thereof, linen, flax, polyethylene, polyaramide, spandex, and wrapped spandex yarns, and any suitable bicomponent or multicomponent fibers. The yarns may be comprised of a single component or a blend of any of the foregoing or any other suitable fibrous materials. Also, multiple ends of yarn which may contain different fibers can potentially be employed to form the knit in the practice of the present invention.

The retentive action of the knit structure can be enhanced if yarns having high elastic recovery, such as rubber, spandex, copolyetheresters, stretch (textured) nylon or other suitable elastomeric yarn, are used.

The knitted retention structure may be formed of knitted material manufactured on standard textile machinery. Potentially useful equipment for fabrication of suitable knitted structures includes knitting machines such as V-bed knitters, circular knitters, warp knitters, or other suitable knitting machines. The fabrication is most easily accomplished on a V-bed type knitter such a Dubled V-bed knitting machine. Such machine can knit tubular articles of appropriate diameter which only need to be sectioned perpendicular to their axial direction (length) to obtain suitable rings or bands which are then usefully employed as a ring-type knitted retention structure. The production of such cylindrical or ring-type retention structures is not limited to V-bed knitters, since specially designed circular knitters could be constructed to knit appropriately dimensioned tubes of knitted material. Furthermore, tubes could be made by knitting larger structures (tubes, flat sheets, ribbons) which then could be cut into strips which are fixed into a circular form by any suitable means.

An illustrative knitted ring embodiment comprises a ring of material approximately 19 millimeters in axial dimension, with an internal lay-flat diameter on the order of 35 millimeters. Such ring may be fabricated on a 7 cut V-bed knitter using approximately 42 needles/side and a stitch length of 13, with a yarn consisting of two ends of 70 denier/34 filament stretch (false-twist textured) nylon 6,6 and one end of approximately 140 denier spandex which has been S, Z wrapped with 2 ends of 70 denier/34 filament nylon 6,6.

As previously mentioned in the "Background of the Invention" section hereof, conventional sheath articles such as condoms employ a resilient, stretchable filament circumscribing the open proximal end of the sheath article, and conventional approaches to providing retention members or elements at the proximal open ends of such articles invariably are directed to the use of such elastic filament or stretchable thermoplastic material such as the thermoplastic elastomers, foam polymers, and hot-melt or pressure-sensitive adhesive materials disclosed in McGlothlin et al U.S. Pat. No. 4,855,169, the salient teachings of which were also discussed in the "Background of the Invention" section hereof. Thus, the entire approach of the prior art to band, collar, or filament retention means has been to form such structural elements out of a continuous structural medium, in the form of a sheet, film, or filament. The prior art has not employed or even proposed knitted materials as materials of construction for retention means for generally tubular sheathing articles. This circumstance is attributable to the logical expectation that knitted web elements when employed to form retention means for a generally tubular sheathing article, would be possessed of inadequate conformability characteristics, and would be characterized by a very low compressive bearing force, inconsistent with the circumferentially and radially inwardly directed compressive action serving to retain the generally tubular sheath on the sheathed part.

In contrast to such logical expectations, however, it has surprisingly been found that knitted web materials may be employed to form retention members, e.g., in the form of a continuous circumferential band or cylindrical collar, or partially circumferentially extending retention element(s), providing a highly efficient level of compressive retention on the sheathed part. In a preferred aspect, the knitted web retention structure employed in the broad practice of the present invention may be quantitatively characterized in terms of various physical test characteristics, Equivalent Diameter Garter Force Value, Mandrel Retention Force Value, and Relaxation Creep Value of specified numerical ranges, as disclosed more fully hereinafter, reflecting preferred effectiveness characteristics for the knitted retention structure.

In the broad practice of the present invention, a knitted retention structure is associated with the sheath member of the sheathing article, at a proximal portion of the sheath member, in the vicinity of its open end, with the knitted retention structure exerting a compressive retaining action on the sheathable part (part to be sheathed) at the proximal portion of the sheath member.

Preferably, the knitted retention structure may comprise a knitted web strip circumferentially extending at least partially about the exterior surface of the sheath member at its proximal portion, e.g., a knitted material band which circumscribes the exterior surface of the sheath member at such proximal portion thereof.

Alternatively, the knitted retention structure may be in the form of circumferentially extending strip(s) of smaller circumferential extent at the circumference of the main sheath portion of the sheathing article. In such arrangement, the partial circumferential strips can be applied to either the exterior or interior surface or to both interior and exterior surfaces of the main sheath portion at the proximal open end of the sheathing article, so that the strips extend transversely to the longitudinal axis of the generally tubular sheathing article, which typically is in elongate form, having a longitudinal axial dimension which may for example be between 4 and 20 times the lay-flat width or transverse dimension of the sheath when reposed on a flat or planar supporting surface. In such fashion, the partial circumferential strip(s) are employed in a "gathered" or "compressed" form which is radially and circumferentially extensible when the part to be sheathed is inserted into the interior volume of the sheath.

In a still further alternative, the knitted web structure may constitute a "skirt" which is joined to and extends proximally away from the proximal open end of the sheath, whereby the knitted skirt member serves as an extension portion of the sheath article, functioning as a neck or collar means for exerting retentive action on the sheath part (proximally at the open end of the sheath portion per se).

Alternatively, the knitted web retention structure may also be configured in any other suitable manner, as for example in the form of criss-crossed strips defining an "X" pattern which is circumferentially deployed on the exterior surface of the proximal portion of the sheathing article.

Additionally, the knitted web retention structure may be internally deployed in the vicinity of the proximal open end of the sheathing article. For example, the knitted web retention structure may comprise a knitted circular band which is bonded to the inner surface of the main sheath portion of the sheathing article, in the vicinity of the proximal open end thereof. The collar may for example be bonded at 90° intervals about the interior surface of the generally tubular article, whereby the sheathing article when spread open for donning, comprises the main sheath portion defining a generally circular cross-section, within which the collar bonded at 90° intervals defines an inscribed square cross-section, within the circular cross-section of the main sheath portion. In such manner, the knitted web structure provides an efficient retentive character, in relation to the sheathed part with which the sheathing article is covered.

The preceding description is illustrative of possible embodiments of the invention, and in place of the four bonding sites at 90° angles, the four bonding sites alternatively could be asymmetrically arranged, e.g., at angles of 110°, 80°, 90° and 80° progressing radially around the sheath, thereby forming a trapezoidal opening; if the sheath is used as a condom, this configuration is more suitably adapted to overfit the glans of the penis. Additionally, the bonding of the knitted material to the interior of the proximal open end of the sheath could be, for example, at three sites, five sites, six sites, or any suitable number of locations and angular positions around the circumference of the sheath which would provide a sufficient opening for donning of the sheath on the part to be sheathed.

Alternatively, the knitted web retention structure may be in the form of a cylindrical band which is bonded to the inner wall of the proximal portion of the main sheath of the sheathing article, so as to provide a gathered or compacted configuration which is radially and circumferentially expandable to permit ingress, into the interior volume of the sheathing article, of the sheathed part. Thereafter, relaxation of the proximal portion of the main sheath part of the sheathing article results in the proximal segment (comprising the knitted web cylindrical band) exerting a compressive and circumferentially applied retaining force on the sheathed part.

It will be apparent from the foregoing discussion that the knitted web retention structure associated with the proximal part of the sheathing article may be configured in a wide variety of forms and structures, as necessary or desirable in a given application to provide the desired retentive action on the part to be sheathed by the sheathing article.

The knitted retention structure may suitably comprise yarn formed of any suitable material of construction, as for example staple yarns, filament yarns, and combinations thereof, such as elastomeric yarn formed of suitable material.

The yarn or fiber stock from which the knitted web structure is formed, may be composed of any suitable material or materials of construction, as for example rubber, spandex, copolyetheresters, texturized nylon, and combinations thereof. More generally, the material of construction of the knitted web retention structure may comprise materials such as acrylics, polyesters, polyamides, rayon, cellulose acetates. silk, wool, cotton, polypropylene, polyurethane, 0opolyetherester, rubber, polyvinyl chloride, polyvinylidene chloride, polyvinyl alcohol, linen, flax, polyethylene, polyaramide, spandex, copolymers and monomers of such polymers, and combinations, composites, and multicomponent forms of the foregoing materials.

The knitting operation by which the knitted web structure is formed may be carried out in any suitable manner, involving needle-knitting with any suitable knitting machines or apparatus conventionally employed to form knitwear. Preferably the knitted retention structure is formed by needle knitting a tube with a "needles per course" characteristic of from about 56 to 110 needles per course, and more preferably from 76 to 90 needles per course, although it is to be recognized that the number of needles per course and the specific needle knitting structure may be widely varied in structure, form and method of manufacturing, within the broad scope of the invention.

In a preferred aspect, the knitted retention structure of the invention may comprise a knitted material structure which is characterized by: an Equivalent Diameter Garter Force Value of from about 0.04 to about 0.06 kilograms at 33 millimeters and from about 0.60 to about 0.90 kilograms at 48 millimeters; a Mandrel Retention Force Value of from about 0.30 to about 0.35 kilograms; and a Relaxation Creep Value from about 10% to about 40% over a range of strains from 30% to 130%. These parametric values are determined by the specific test procedures set out below.

The Equivalent Diameter Garter Force Value is determined by constructing a ring of the knitted material, as for example may be produced by a V-bed knitting machine to produce a tubular knitted body, following which the knitted tubular structure is transversely sectioned (transverse to its longitudinal axis) to form a flat cylindrical band element. This ring of knitted material is of the specific dimensions (diameter, thickness, and axial length) characteristic of the actual knitted ring employed as the retention structure, when a flat cylindrical retention structure is employed. The test also is employed for corresponding testing of knitted materials used in other forms (i.e., forms other than cylindrical bands or rings) of the actual retention structure.

In the test, the knitted ring with its associated sheath is placed over two rollers each having a diameter of 3 millimeters. The rollers are separated to a distance of 60 millimeters between their centers, with stretching of the knitted ring, at which point the force is measured. The Equivalent Diameter of the stretched ring is given by the equation:

Equivalent Diameter = (3 millimeters × $\pi$ + 60 millimeters × 2)$\pi$ and from this Equivalent Diameter the stretching force is identified as a force value at the specified diameter of the initial starting ring, this numerical value constituting the Equivalent Diameter Force Value, in kilograms of stretching force at a specified diameter of the starting ring of the knitted material retention structure.

The Mandrel Retention Force Value is a measure of sliding frictional force exerted on a mandrel by a generally tubular sheathing article with a retention structure at its proximal end, and is measured as the sheathing article is pulled off of the mandrel. Experimentally, a 41 millimeter diameter polished aluminum mandrel is placed upright on a vertically translatable platform. A sheathing article is unrolled over the mandrel, from an initial rolled conformation, so that the unrolled sheathing article extends vertically downward on the mandrel for a distance (covered length dimension) of 125 millimeters. In this mandrel-covering form, the closed distal end of the sheathing article is attached to a force gauge. The platform then is translated downwardly at a rate of 250 millimeters per minute, and the maximum force necessary to remove the sheathing article from the mandrel is recorded, as the Mandrel Retention Force Value, in kilograms.

The Relaxation Creep Value is a measure of how much a knitted retention structure material deforms over time when it is placed in a strained state. In this procedure for determining Relaxation Creep Value, a strain of from about 30% to 130% is imposed on cylindrical bands of the knitted material by placing the bands over mandrels of various diameter (outer diameter). The mandrels are placed in a forced air oven for 7 days at 70° C., bearing the knitted rings thereon, in order to simulate long-term aging of the rings in a rolled, packaged configuration. The mandrels then are removed from the oven and allowed to cool for at least one hour. The knitted bands then are removed from the mandrel and allowed to relax for one minute, at which time their internal diameter is measured. The percent creep then is calculated as a function of the percent strain initially imposed on the ring, using the following equations:

$$\% \text{ strain} = \frac{\text{Mandrel Outer Diameter} - \text{Initial Knitted Ring Inner Diameter)}}{\text{Initial Knitted Ring Inner Diameter}} \times 100$$

$$\% \text{ Creep} = \frac{\text{(Final Knitted Ring Inner Diameter} - \text{Initial Knitted Ring Inner Diameter)}}{\text{Initial Knitted Ring Inner Diameter}} \times 100$$

The results obtained by calculation using the above equations then may be plotted with percent creep as a function of percent strain, and the resulting empirical data is employed to determine values of creep over a strain range of from about 30% to 130%, providing the Relaxation Creep Value of a specific percentage range of values over such strain range of 30% to 130%.

The sheath portion of the sheathing article of the present invention may be formed of any suitable material, and preferably is of an elastic flexible material which is readily deformable (stretchable) in the donning operation involving sheathing of the sheathed part, without tearing, breaking, or other adverse affect on the structural integrity of the sheathing article. By way of illustration, the sheath may be formed of a material of construction such as: polyurethanes; latex rubbers; silicone elastomers; ethylene-propylene thermoplastic elastomers; styrene block copolymer thermoplastic elastomers; olefinic thermoplastic elastomers; polyether block amide thermoplastic elastomers; polyvinyl chlorides; and acrylic-based thermoplastic elastomers.

The sheath preferably is formed of a thin film material, particularly in applications such as condoms and prophylactic articles. The film may have a relatively low thickness character, as for example from about 0.01 millimeters to 2 millimeters, depending on the specific end use application to which the sheathing article is to be applied. In condom or surgical glove applications, for example, the thickness of the sheath may be on the order of 0.01 millimeters to about 0.1 millimeters, preferably from about 0.02 to about 0.05 millimeters. A preferred class of sheath materials is thermoplastic elastomers, such as polyurethanes or block copolymers.

Preferred polyurethanes include thermoplastic, primarily linear polyurethanes, and the polyurethanes useful in the broad practice of the present invention comprise both polyether-based and polyester-based polyurethanes, as well as those based on a combination of both polyether and polyester types. The polyurethanes may be in the form of block copolymers, and the polyurethanes may be formed of a wide range of precursor (reactant) materials including a wide variety of polyisocyanates and polyurethane-forming co-reactants therewith, e.g., polyols.

Preferred block copolymer materials include those comprising hard and soft segments wherein the soft segment component has a glass transition temperature below 25° C. and the hard segment component is shorter and stiffer in character with a glass transition temperature above 25° C. Various rubber-based copolymers of such type are known and potentially useful in the broad practice of the invention. Specific materials which may be usefully employed in some instances include the rubber-based block copolymers commercially available under the trademark Kraton ® (Shell Chemical Company, Houston, Tex.).

Concerning the dimensional characteristics of knitted ring retention structures, i.e., retention structures formed of a knitted material in the form of a continuous cylindrical element, the thickness of the knitted material may for example be on the order of from 0.2 to 5 millimeters, and more preferably from about 0.5 to about 4 millimeters. The length or axial direction dimension of the ring may be of any suitable dimension consistent with the overall dimensions of the sheath with which the knitted retention structure is associated; in condom and prophylactic article applications, the knitted retention ring may for example have a length (axial dimension) of from about 5 millimeters to about 50 millimeters and more preferably from about 15 millimeters to 30 millimeters. The diameter of the ring when employed in a cylindrical ring conformation will also depend on the corresponding dimensions of the sheathing article with which the retention structure is employed; in condom and prophylactic article applications, the knitted ring diameter may for example range from 25 millimeters to about 55 millimeters, more preferably in the range of from about 30 millimeters to about to about 50 millimeters.

As an illustrative example of a condom article usefully employed in the practice of the present invention, in a specific embodiment thereof, the elongate sheath of the condom article may be formed from Elastollan ® thermoplastic polyurethane resin (BASF Corporation (Parsippany, N.J.)) having a thickness of about 25 microns. The sheath in such embodiment may have a generally tubular shape, with a diameter (measured with the condom in lay-flat position in a planar surface) of 75 millimeters, and with a length of approximately 22 centimeters. The knitted ring may be formed of a spandex fiber needle knitted material, wherein the spandex has been S, Z wrapped with nylon, 6, 6, and may have a cylindrical ring conformation with an axial length dimension of approximately 2 cm, a diameter of approximately 25 millimeters, and a thickness of approximately 1.2 millimeters.

The invention will now be more fully described in terms of various illustrative embodiments thereof, as shown in the drawings.

Figure 1:
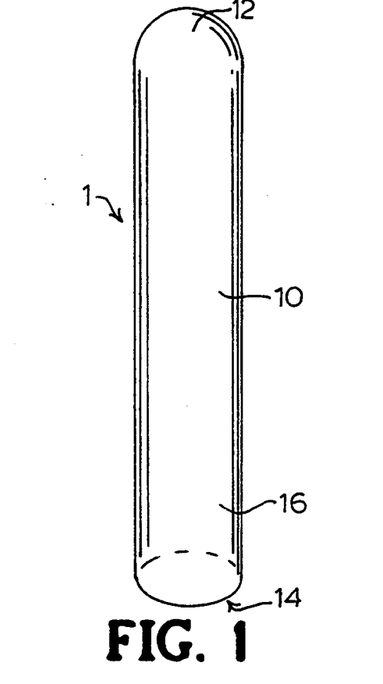
FIG. 1 is a perspective view of a sheath member employed to form a sheathing article, according to one embodiment of the invention.

FIG. 1 is a perspective view of a generally tubular sheath article 1 comprising a main sheath portion 10 having an open proximal end 14 at its proximal portion 16 and a closed distal end 12. The main sheath portion 10 may suitably be formed of a polyurethane thin film material, being of a size appropriate to usage as a condom or prophylactic article, i.e., for closely overfitting a human penis.

Figure 2:
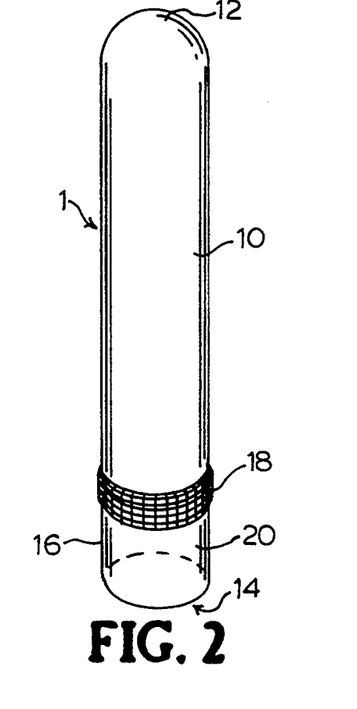
FIG. 2 is a perspective view of the FIG. 1 sheath member having a knitted fabric band circumscribing a proximal part of the sheath exterior surface.

FIG. 2 shows the sheathing article, having its constituent parts number correspondingly with respect to FIG. 1, with a knitted retention band 18 disposed on an exterior surface at the proximal portion 16 of the condom, whereby a proximal skirt 20 is extended proximally from the part of the sheath circumscribed by the knitted retention ring 18.

The knitted retention ring 18 may for example be formed of a needle-knitted tubular material having a needles per course characteristic of from 50 to 100 needles per course, and formed of a yarn consisting of two ends of false-twist textured nylon and one end of spandex, wherein the spandex yarn may be S, Z wrapped with nylon.

Figure 3:
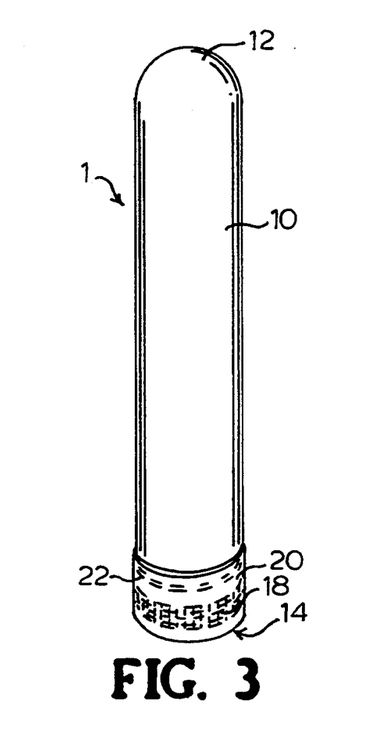
FIG. 3 is a perspective view of the sheath member of FIGS. 1 and 2, with the knitted fabric band enclosed by an everted skirt portion of the sheath member, to provide a sheathing article according to one embodiment of the invention.

The sheathing article 1 is shown in FIG. 3 as a finished article, wherein the skirt portion 20 of the main sheath is everted over the knitted retention ring 18 and sealed, as by heat seal 22 to the main sheath, whereby the everted and overlapped portion 20 of the sheath forms a pocket or enclosure containing the knitted retention ring 18. By this simple structure, a finished sheathing article 1 is formed, which is amenable to use as a condom or prophylactic article. For example, the sheathing article 1 shown in FIG. 3 may be rolled from the proximal end to the distal end thereof in a conventional fashion, utilizing the knitted ring structure 18 as a "rolling core" on which successive layers of main sheath film material are built up as the rolling proceeds, and whereby in final rolled form the resulting toroidal roll circumscribes the distal end 12 of the sheathing article, so that in subsequent use, the rolled sheathing article may be disposed on the glans of the penis and unrolled from the glans to the base of the penis, for sheathing of the male member for subsequent protected coital activity.

Figure 4:
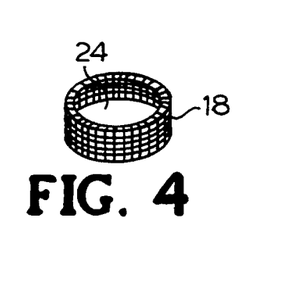
FIG. 4 is a perspective view of the knitted fabric band of FIG. 2.
Figure 5:
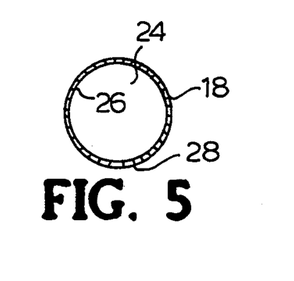
FIG. 5 is a top plan view of the knitted fabric band of FIG. 2.

FIG. 4 is a perspective view of the knitted retention ring 18 which as shown is of cylindrical form, with an interior opening 24 being circumscribed by the ring structure. A corresponding top plan view is shown in FIG. 5, wherein all parts and features are numbered correspondingly with respect to FIG. 4. As shown in FIG. 5, the knitted retention ring has an inner surface 26 which in application to a sheath in the manner shown in FIGS. 2 and 3, bears compressively against the exterior surface of the sheath. The ring also features an exterior surface 28 which is exteriorly presented when the retention ring is deployed in a circumscribing fashion on the exterior surface of the sheath, as for example is shown in FIGS. 2 and 3.

Figure 6:
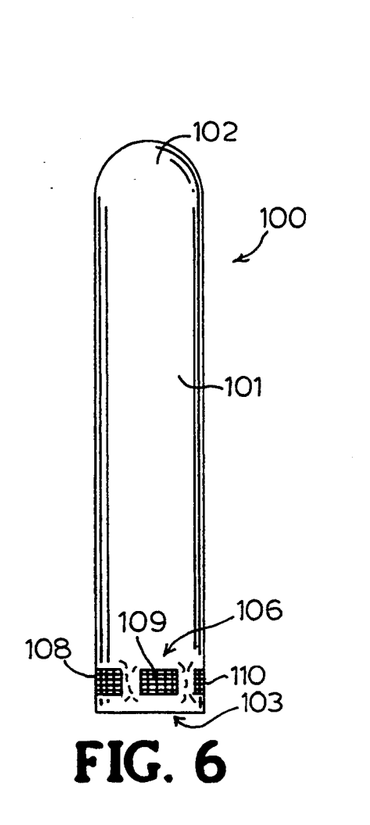
FIG. 6 is a perspective view of a sheathing article according to another embodiment of the invention.

FIG. 6 is a perspective view of a sheathing article 100 according to another embodiment of the invention. This sheathing article comprises a main sheath 101 having an open proximal end 103 and a closed distal end 102. At the proximal portion 106 of the sheath there is disposed a series of circumferentially spaced-apart knitted retention elements 108, 109, and 110, each of which is bonded in a stretched condition to the exterior surface at the proximal end 106 of the sheath. Subsequent to the completion of the bonding operation and relaxation of the tensioned retention elements 108, 109, and 110, the proximal portion 106 of the sheath is circumferentially gathered in a contracted state, which after sheathing of the penis permits the proximal portion 106 (under the impetus of the knitted retention elements) to bear compressively against the base of the penis.

Figure 7:
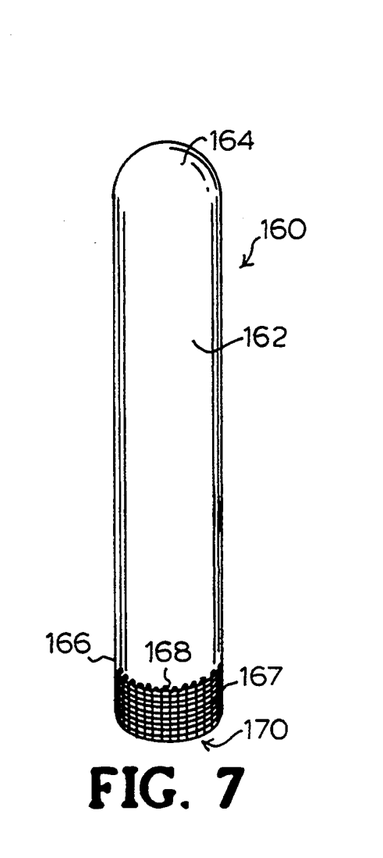
FIG. 7 is a perspective view of yet another sheathing article embodiment of the invention.

FIG. 7 is a perspective view of a sheathing article 160 according to another embodiment of the present invention. This sheathing article comprises a generally tubular main sheath 162 having a closed distal end 164 and a proximal end 166 to which knitted retention ring 167 is joined by sewn seam 168, to thereby form a knitted extension skirt for the sheath 162 having an open proximal opening 170. By this structure, a knitted retention ring is provided which may be circumferentially and radially outwardly stretched in the donning operation, to admit the penis into the interior volume of the sheathing article, following which, upon relaxation of the knitted retention structure 167, the same bears compressively against the base of the penis, for enhanced and comfortable retention of the sheathing article on the penis of the wearer.

Figure 8:
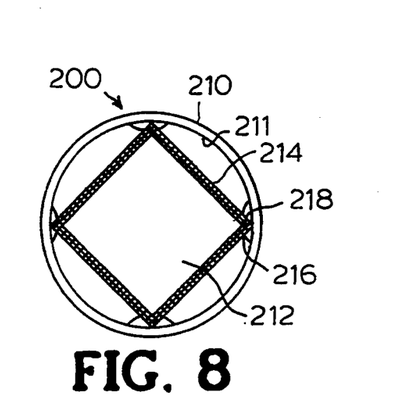
FIG. 8 is a bottom plan view of a sheathing article according to still another embodiment of the invention.

FIG. 8 is a bottom plan view of a sheathing article 200 according to another embodiment of the present invention. As shown in the drawing, the sheathing article comprises generally tubular main sheath portion 210 having an interior surface 211 bounding the interior volume 212 within the sheathing article. A knitted retention structure 214 is bonded by bonding medium 218 to the inner surface 211 of the main sheath portion 210, at 90° intervals about the circumference of the inner surface 211. In this manner, the knitted retention structure 214 describes, in cross-section, an inscribed square conformation relative to the generally circular cross-section of the sheath 210 per se. By this arrangement, the knitted retention structure is capable of expansion (toward engagement with the inner surface 211) between the bonded pieces of the retention structure during donning of the sheathing article 200, with the knitted retention structure 214 subsequently effecting a retentive action on the sheathed part.

Figure 9:
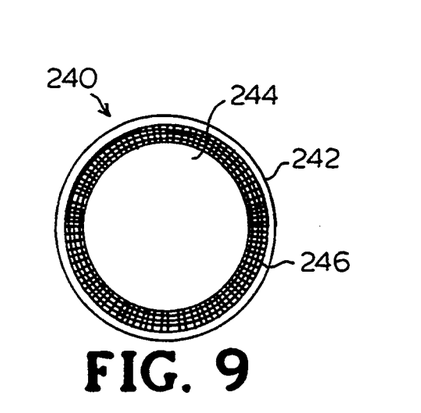
FIG. 9 is a bottom plan view of yet another sheathing article embodiment of the invention.
Figure 10:
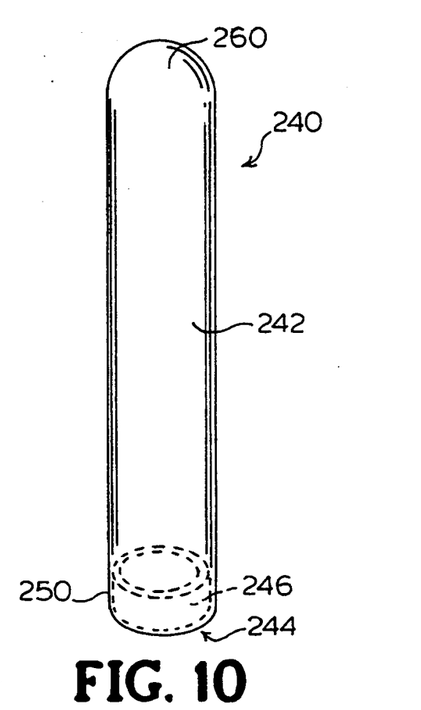
FIG. 10 is a perspective view of the sheathing article shown in bottom plan view in FIG. 9.

FIG. 9 is a bottom plan view of a sheathing article 240 according to another embodiment of the invention, comprising sheath 242, within which is disposed knitted retention ring 246 circumscribing the interior volume 244 within the sheath. The knitted retention structure 246 in such embodiment may be bonded, sewn, or otherwise affixed to the inner surface of the sheath, as desired. FIG. 10 is a perspective view of the sheathing article 240 shown in bottom plan view in FIG. 9, wherein the corresponding parts of FIGS. 9 and 10 are correspondingly numbered. As shown in FIG. 10, the sheathing article 240 comprises an elongate, generally tubular sheath 242 having a closed distal end 260 and an open proximal end 244. Within the proximal end portion 250 of the sheath is interiorly disposed the knitted retention structure 246, which as mentioned may be suitably affixed to the inner surface of the sheath.

Figure 11:
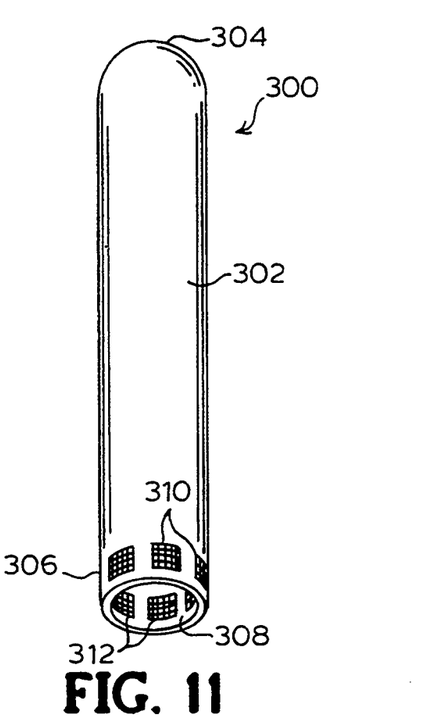
FIG. 11 is a perspective view of a sheathing article according to another embodiment of the invention.

FIG. 11 is a perspective view of a sheathing article according to another embodiment of the invention. As shown in the drawing, the sheathing article 300 includes a main tubular sheath 302 having a closed distal end 304 and a proximal end 308 which is open for receipt of the member to be sheathed within the interior volume bounded and defined by the sheath 302.

At the proximal portion 306 of the sheath, is exteriorly arranged a series of circumferentially spaced-apart knitted retention elements 310, and a series of interiorly disposed, circumferentially spaced-apart knitted retention elements 312, wherein the exterior retention elements 310 are in radial alignment with corresponding interior retention elements 312. Each of the interior and exterior retention elements is bonded in a stretched condition to appertaining surface portions of the proximal end 306 of the sheath. Subsequent to completion of bonding operation and relaxation of the tensioned retention elements 310 and 312, the proximal portion 306 of the sheath is circumferentially gathered in a contracted state, which after sheathing of the penis permits proximal portion 306 to bear compressively against the base of the penis.

Figure 12:
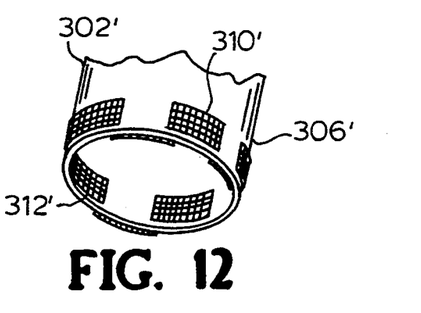
FIG. 12 is a perspective view of a proximal portion of a sheathing article according to a further embodiment of the invention.

FIG. 12 is a perspective view of a portion of a sheathing article according to another embodiment of the invention, wherein the sheath 302' at its proximal portion 306' has circumferentially spaced-apart exterior retention elements 310' which are overlappingly disposed on the exterior surface of the sheath in relation to an interior array of spaced-apart retention elements 312', wherein each exterior element 310' circumferentially overlaps two of the interior retention elements 312', and correspondingly, each of the interior retention elements 312' overlaps two of the exterior retention elements 310'. This sheathing article may be fabricated in a manner analogous to that described hereinabove with respect to the FIG. 11 sheathing article.

Figure 13:
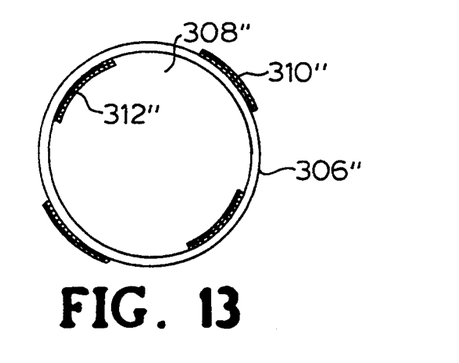
FIG. 13 is a bottom plan view of a sheathing article according to yet another embodiment of the invention.

A still further embodiment of the invention is shown in FIG. 13, which is a bottom plan view of a sheathing article whose proximal portion 306" circumscribes an open proximal end of the sheathing article, so that the sheath bounds an interior volume 308" therewithin. On the exterior surface of the proximal portion 306" is disposed circumferentially spaced-apart retention elements 310" and on the interior surface of the proximal portion 306" is disposed circumferentially spaced-apart retention elements 312". In the arrangement shown, the interior and exterior retention elements are off-set in relation to one another, to provide a further variation to the interior/exterior retention element arrangements of the embodiments shown and described with reference to FIGS. 11 and 12 hereof.

The features and advantages of the invention are more fully shown with respect to the following example, which are to be non-limitingly construed, as regards the broad scope and varying embodiments of the invention.

EXAMPLE

Equivalent Diameter Garter Force Values were determined by the test procedure identified hereinabove, for the following ring (cylindrical band) samples: a latex rubber ring cut from an unlubricated latex rubber condom (sample 1); a band portion cut from a skin (caecum) condom (sample 2); a 76 needles per course knitted band sealed inside a polyurethane condom sheath in the manner of the sheathing article shown in FIG. 3 hereof (sample 3); a 84 needles per course knitted band sealed inside a polyurethane condom sheath in the manner of the sheathing article of FIG. 3 herein (sample 4); and a 90 needles per course knitted band sealed inside a polyurethane condom sheath in the manner of the sheathing article shown in FIG. 3 hereof (sample 5). Samples 3–5 utilized knitted bands formed of nylon fiber and spandex fiber which was S, Z wrapped with nylon 6,6.

The Equivalent Diameter Garter Force measured in this test provides a measurement of the comfort of the retention ring in application to a condom sheathing article, since the retention structure in such article will be disposed positionally at the base of the penis, and the retention force will thereby correlate to the retention efficacy of the knitted retention ring and its comfort to the wearer.

A table of Garter Force Measurements at specific mandrel diameters is set out in Table I below, representing a majority of erect penis sizes.

TABLE I

| Sample No. | Force (kg) at a specific diameter (millimeters) | | |
|---|---|---|---|
| | 33 millimeters | 41 millimeters | 48 millimeters |
| 1 | 0.00 | — | 0.34 |
| 2 | 0.03 | — | 0.40 |
| 3 | 0.05 | 0.27 | 0.69 |
| 4 | 0.04 | 0.24 | 0.65 |

TABLE I-continued

| | Force (kg) at a specific diameter (millimeters) | | |
|---|---|---|---|
| Sample No. | 33 millimeters | 41 millimeters | 48 millimeters |
| 5 | 0.05 | 0.31 | 0.84 |

As shown by the data in Table I, the knitted rings at (Samples 3-5) have an advantage over latex rubber (Sample 1) and skin condoms (Sample 2) at lower diameters, since the knitted rings can provide a small measure of Garter Force to hold the condom on the flaccid penis after detumescence. Further, comfort of sheathing articles comprising the knitted rings in condom applications is improved, since the force (Garter Force) of the knitted band, although slightly greater, is spread over a wider area than in the skin and latex rubber condoms.

Next, Mandrel Retention Force Values were determined by the method previously described herein, for samples corresponding to those of Sample Nos. 2-5 of Table I. The aforementioned procedure for determining Mandrel Retention Force Value was carried out, and the maximum force necessary to remove the condom from the polished aluminum mandrel is identified in Table II for each of these samples.

TABLE II

| Sample No. | Max Force (kg) |
|---|---|
| 2 | 0.28 |
| 3 | 0.32 |
| 4 | 0.31 |
| 5 | 0.33 |

As shown by the data in Table II, the retention force was greater for the knitted bands of samples 3-5 than the skin condom of Sample 2. As a result, the condoms with the knitted band will be less prone to slippage than skin condoms of the type represented by Sample 2. Note that in this test, no retention force values were determined for latex rubber rings corresponding to Sample No. 1 in Table I, for the reason that such latex rubber condom rings could not be pulled from the mandrel without tearing or breakage of same.

Relaxation Creep Values then were determined by the experimental procedure previously described herein for three different knitted rings formed of nylon fibers and spandex fibers which had been S,Z wrapped with nylon 6,6. Sample A comprised a knitted ring formed of needle knitted fabric with a characteristic of 76 needles per course. Sample B was of the sample material of construction, but with a needles per course characteristic of 84 needles per course. Sample C was of the same material of construction of Samples A and B, but had a needles per course characteristic of 90 needles per course.

Figure 14:
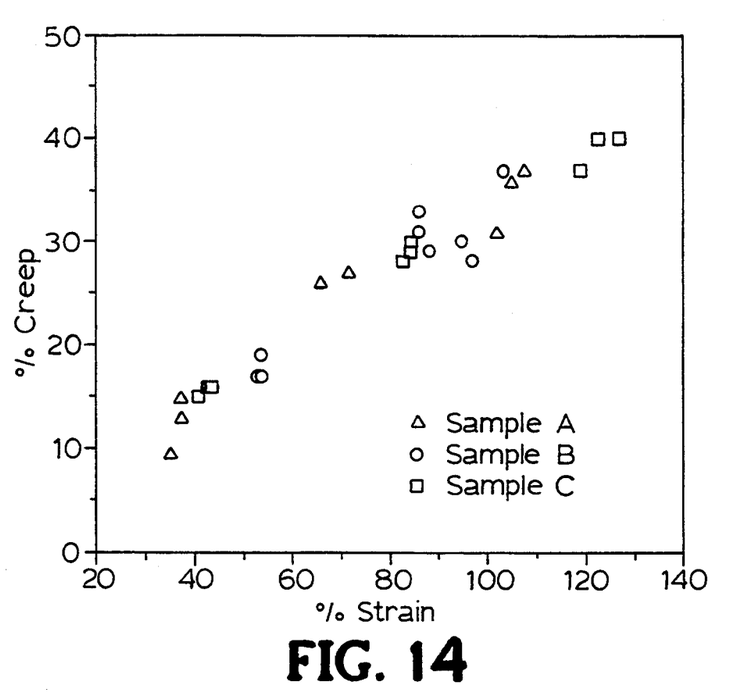
FIG. 14 is a graph of percent creep as a function of percent strain, for knitted ring elements potentially usefully employed as knitted retention structures in the practice of the present invention.

The percent creep and percent strain values were determined in accordance with the previously described equations and procedure, and the results were plotted as a percent creep/percent strain graph, as shown in FIG. 14.

The data plotted in FIG. 14 show that the three different knitted rings behaved similarly in their creep characteristics. In addition, such creep behavior of the knitted ring samples was independently determined to be comparable to the creep characteristics of latex rubber rings representative of conventional latex rubber condoms.

While the invention has been described with respect to specific aspects, features, and embodiments, it will be appreciated that numerous creations, modifications and other embodiments exist, and accordingly the invention is to be broadly construed as regards such modifications, variations, and embodiments.

What is claimed is:

1. A sheathing article for protective covering of a sheathable part, comprising:
   (i) a generally tubular sheath member having a closed first end and an open second end defining an enclosed interior volume within the sheath member, accessible by the open second end, for introduction of the sheathable part into the interior volume through the open second end;
   (ii) a knitted retention structure associated with the sheath member at a proximal portion thereof in the vicinity of its open second end, for exerting a compressive retaining action on the sheathable part at the proximal portion of the sheath member, said knitted retention structure comprising a knitted material band circumscribing the exterior surface of the sheath member at its proximal portion, and
   (iii) a circumferentially extending proximal compartment at the proximal portion of the sheath member, wherein the proximal compartment comprises an exteriorly everted skirt segment of the sheath member, secured to the exterior surface of the sheath member to define an internal compartment volume containing the knitted material band.

2. An article according to claim 1, wherein said knitted material band has a diameter of from about 25 millimeters to about 55 millimeters. and wherein the sheathing article is of a size adapted for sheathing of a penis.

3. A sheathing article for protective covering of a sheathable part, comprising:
   (i) a generally tubular sheath member having a closed first end and an open second end defining an enclosed interior volume within the sheath member, accessible by the open second end, for introduction of the sheathable part into the interior volume through the open second end; and
   (ii) a knitted retention structure associated with the sheath member at a proximal portion thereof in the vicinity of its open second end, for exerting a compressive retaining action on the sheathable part at the proximal portion of the sheath member, wherein the knitted retention structure comprises a knitted band characterized by: an Equivalent Diameter Garter Force Value of from about 0.04 to 0.06 kilogram at 33 millimeters and from about 0.60 to about 0.90 kilogram at 48 millimeters; a Mandrel Retention Force Creep Value of from about 0.30 to about 0.35 kilogram; and a Relaxation Creep Value of from about 10% to about 40% over a strain range of from 30% to 130%.

4. An article according to claim 3, wherein the knitted retention structure comprises a knitted web strip circumferentially extending at least partially about the exterior surface of the sheath member at its proximal portion.

5. An article according to claim 3, wherein the knitted retention structure comprises yarn selected from the group consisting of: staple yarns, filament yarns, and combinations thereof.

6. An article according to claim 3, wherein the knitted retention structure comprises elastomeric yarn.

7. An article according to claim 6, wherein elastomeric yarn is formed of a material selected from the group consisting of rubber, spandex copolyetheresters, texturized nylon, and combinations thereof. needles per course.

8. An article according to claim 3, wherein the knitted retention structure comprises yarn formed of a material selected from the group consisting of: acrylics; polyesters; polyamides; rayon; cellulose acetates; silk; wool; cotton; polypropylene; polyurethane; copolyetherester; rubber; polyvinyl chloride; polyvinylidene chloride; polyvinyl alcohol; linen; flax; polyethylene; polyaramide; spandex; compolymers of monomers of said polymers; and composites, combinations and multicomponent forms thereof.

9. An article according to claim 3, wherein the knitted band comprises a needle knitted material having a needles per course characteristic of from 56 to 110 needles per course.

10. An article according to claim 3, wherein the knitted retention structure comprises a yarn consisting of two ends of false-twist textured nylon and one end of spandex.

11. An article according to claim 10, wherein the spandex yarn is S, Z wrapped with nylon.

12. An article according to claim 3, wherein the knitted band has a diameter of from about 25 millimeters to about 55 millimeters, and wherein line sheathing article is of a size adapted for sheathing of a penis.

13. A method of making a sheathing article, comprising:
   (a) providing a generally tubular sheath member having a closed first end and an open second end;
   (b) disposing a circumferentially extending knitted retention band about an exterior surface of the second end portion of the sheath member, in spaced relation to the open second end thereof, to thereby define a proximal segment of the sheath member between the knitted retention band and the open second end;
   (c) everting the proximal segment of the sheath member between the knitted retention band and the open second end so that the everted proximal segment enclosingly overlies the knitted retention band; and
   (d) securing the everted proximal segment of the sheath member to an overlaid exterior surface region of the sheath member, to form an enclosure volume containing the knitted retention band.

14. The method of making a sheathing article according to claim 13, wherein said securing of the everted proximal segment of the sheath member to an overlaid exterior surface of the sheath comprises heat sealing of the everted proximal segment of the sheath member to an overlaid exterior surface of the sheath.

* * * * *

UNITED STATES PATENT AND TRADEMARK OFFICE
CERTIFICATE OF CORRECTION

PATENT NO. : 5,361,779
DATED : November 8, 1994
INVENTOR(S) : Wilson III, Thomas W.

It is certified that error appears in the above-indentified patent and that said Letters Patent is hereby corrected as shown below:

Column 1, line 5, insert the following information:

-- <u>GOVERNMENT LICENSE RIGHTS</u>

The invention claimed herein was made under one or more of the following contracts: U.S. Agency for International Development Contract Nos. DPE-3041-A-00-0043 and DPE-0537-A-00-4047, and National Institutes of Heal Contract No. N01-HD-2-3143, and the U.S. Government has certain rights therein. --

Signed and Sealed this

Eighteenth Day of March, 1997

Attest:

*Attesting Officer*

BRUCE LEHMAN

*Commissioner of Patents and Trademarks*